Charbonneau et al.

[11] Patent Number: 4,886,658
[45] Date of Patent: Dec. 12, 1989

[54] ORAL TREATMENT METHOD FOR REDUCING PLAQUE WITH REDUCED STAINING

[75] Inventors: Duane L. Charbonneau, Middletown; Debra J. Moore; Joel I. Shulman, both of Cincinnati, all of Ohio

[73] Assignee: The Procter & Gamble Company, Cincinnati, Ohio

[21] Appl. No.: 284,262

[22] Filed: Dec. 14, 1988

[51] Int. Cl.[4] .................... A61K 7/16; A61K 7/20; A61K 7/22
[52] U.S. Cl. .................................. 424/53; 424/54
[58] Field of Search ..................... 424/49, 53, 54

[56] References Cited

U.S. PATENT DOCUMENTS

| | | | |
|---|---|---|---|
| Re. 31,397 | 9/1983 | Rodon | 424/54 |
| 2,684,924 | 7/1954 | Rose et al. | 414/326 |
| 2,830,006 | 4/1958 | Birtwell et al. | 252/106 |
| 2,863,919 | 12/1958 | Birtwell et al. | 260/565 |
| 2,990,425 | 6/1961 | Senior | 260/501 |
| 3,075,921 | 1/1963 | Brocklehurst et al. | 252/99 |
| 3,468,898 | 9/1969 | Cutler et al. | 260/301 |
| 3,925,543 | 12/1975 | Donohue | 424/54 |
| 3,934,002 | 1/1976 | Haefele | 424/54 |
| 3,937,805 | 2/1976 | Harrison | 424/52 |
| 3,937,807 | 2/1976 | Haefele | 424/52 |
| 3,957,967 | 5/1976 | L'Orange | 424/48 |
| 3,988,433 | 10/1976 | Benedict | 424/53 |
| 4,051,234 | 9/1977 | Gieske et al. | 424/52 |
| 4,059,687 | 11/1977 | Bauman | 424/54 |
| 4,080,441 | 3/1978 | Gaffar et al. | 424/54 |
| 4,118,474 | 10/1978 | Gaffar et al. | 424/54 |
| 4,256,731 | 3/1981 | Curtis et al. | 424/54 |
| 4,273,759 | 6/1981 | Gaffar et al. | 424/54 |
| 4,490,269 | 12/1984 | Gallopo | 252/94 |
| 4,670,252 | 6/1987 | Sampathkumar | 424/53 |
| 4,716,035 | 12/1987 | Sampathkumar | 424/52 |

FOREIGN PATENT DOCUMENTS

| | | |
|---|---|---|
| 0027693 | 4/1981 | European Pat. Off. |
| 0066992 | 12/1982 | European Pat. Off. |
| 0133354 | 2/1985 | European Pat. Off. |
| 1365030 | 8/1974 | United Kingdom |
| 1378671 | 12/1974 | United Kingdom |

Primary Examiner—Shep K. Rose
Attorney, Agent, or Firm—Milton B. Graff, IV; Jack D. Schaeffer; Richard C. Witte

[57] ABSTRACT

The present invention relates to methods for treating or preventing dental plaque, caries, or gingival or periodontal diseases of the oral cavity in humans or lower animals, with reduced staining of teeth or dentures. The methods comprise topically applying to the oral surfaces of the teeth or dentures of the humans or lower animals:

(a) a safe and effective amount of a monoperoxyphthalate compound, and (b) a safe and effective amount of an anti-plaque bisbiguanide compound.

The present invention also relates to compositions for achieving such treatments.

23 Claims, No Drawings

ORAL TREATMENT METHOD FOR REDUCING PLAQUE WITH REDUCED STAINING

TECHNICAL FIELD

The present invention relates to methods for reducing dental plaque, caries, or gingival or periodontal diseases, especially methods for enhancing the efficacy and reducing the staining tendencies of bis-biguanide antiplaque compounds.

BACKGROUND OF THE INVENTION

It has long been known that certain bis-biguanide compounds can be used in oral germicidal compositions: U.K. Pat. Specification No. 1,365,030 of Merck & Co., Inc. published on Aug. 29, 1974. As such, these compounds cause some inhibition of the formation of dental plaque. However, such compounds do not completely inhibit the formation of dental plaque; there is substantial opportunity for improving such efficacy of these compounds.

It is also well known that certain bis-biguanide compounds, when used as anti-plaque agents, cause unslightly staining of teeth. Many procedures have been proposed to reduce such tooth staining: U.S. Pat. Nos. 3,925,543 issued to Donohue on Dec. 9, 1975; 3,934,002 issued to Haefele on Jan. 20, 1976; 3,937,805 issued to Harrison on Feb. 10, 1976; 3,937,807 issued to Haefele on Feb. 10, 1976; 3,957,967 issued to L'Orange on May 18, 1976; 4,051,234 issued to Gieske and Juneja on Sept. 27, 1977; 4,080,441 issued to Gaffar, deVries and Carroll on Mar. 21, 1978; 4,118,474 issued to Gaffar and Niles on Oct. 3, 1978; 4,183,916 issued to Rhodon on Jan. 15, 1980 (and corresponding Re. 31,397 reissued on Sept. 27, 1983); 4,256,731 issued to Curtis and Bhargava on Mar. 17, 1981; and 4,273,759 issued to Gaffar and Gaffar on June 16, 1981.

Although the above methods may reduce the tooth stain caused by the bis-biguanide compounds, better methods for further reducing such stain are highly desirable.

Peroxy compounds, including monoperoxyphthalic compounds, have been used for preventing or removing stains from teeth or dentures: U. S. Pat. Nos. 3,988,433 issued to Benedict on Oct. 26, 1976; 4,273,759 issued to Gaffar and Gaffar on June 16, 1981; 4,490,269 issued to Gallopo on Dec. 25, 1984; and European Pat. Application No. 0,133,354 of Interox Chemicals, Ltd., published Feb. 20, 1985. Monoperoxyphthalic acid compounds have also been disclosed in anti-gingivitis compositions: U.S. Pat. Nos. 4,670,252 issued to Sampathkumar on June 2, 1987; and 4,716,035 issued to Sampathkumar on Dec. 29, 1987.

It is an object of the present invention to provide a method for reducing or inhibiting the formation of plaque on dental surfaces by treating such dental surfaces, in part, with a bis-biguanide compound.

It is a further object of the present invention to provide an enhanced reduction in plaque compared to that normally achieved by treatment with such a bis-biguanide compound.

It is a still further object of the present invention to achieve such enhanced reduction of plaque with substantially less staining of teeth than normally occurs during treatment with such a bis-biguanide compound.

SUMMARY OF THE INVENTION

The present invention relates to methods for treating or preventing dental plaque, caries, or gingival or periodontal diseases of the oral cavity in humans or lower animals, with reduced staining of teeth or dentures, said method comprising topically applying to the oral surfaces of the teeth or dentures of humans or lower animals:
(a) a safe and effective amount of a monoperoxyphthalate compound, and
(b) a safe and effective amount of an anti-plaque bis-biguanide compound.

DETAILED DESCRIPTION OF THE INVENTION

The present invention involves the use of anti-plaque bis-biguanide compounds. As used herein, anti-plaque bis-biguanide compounds are those bis-biguanide compounds having anti-plaque activity which have the structure:

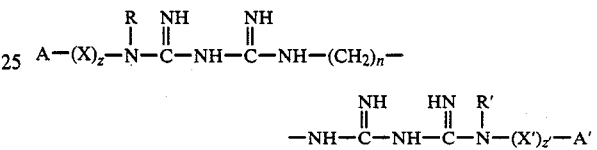

wherein A and A' each represent either (1) a phenyl radical which optionally is substituted by an alkyl or alkoxy group containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein z and z' each can be either 0 or 1; wherein R and R' each represent either hydrogen, an alkyl radical containing from 1 to about 12 carbon atoms, or an aralkyl radical containing from 7 to about 12 carbon atoms; wherein n is an integer from 2 to 12 inclusive; and wherein the polymethylene chain $(CH_2)_n$ may optionally be interrupted by oxygen or sulfur atoms, aromatic nuclei, etc. The salts of the above compounds are especially desirable. Water-soluble salts include the acetate, the hydrochloride, and especially the gluconate salt of the above compounds. Such compounds have been disclosed in the following U.S. Pat. Nos. which are hereby incorporated by reference: 2,684,924 issued to Rose and Swain on July 27, 1954; 2,990,425 issued to Senior on June 27, 1961; 2,830,006 issued to Birtwell and Rose on Apr. 8, 1958; 2,863,919 issued to Birtwell and Rose on Dec. 9, 1958; 3,468,898 issued to Cutler and Schalit on Sept. 23, 1969; and 4,059,687 issued to Bauman on Nov. 22, 1977.

Examples of bis-biguanide compounds useful in the present invention include the following:
1,6-bis-(2-ethylhexylbiguanidohexane) dihydrochloride; 1,6-di-($N_1$, $N_1'$-phenyldiguanido-$N_5,N_5'$)-hexane tetrahydrochloride; 1,6-di-($N_1$, $N_1'$-phenyl-$N_1,N_1'$-methyldiguanido-$N_5,N_5'$)-hexane dihydrochloride; 1,6-di-($N_1$, $N_1'$-o-chlorophenyldiguanido-$N_5,N_5'$)-hexane dihydrochloride; 1,6-di($N_1,N_1'$-2,6-dichlorophenyldiguanido-$N_5$,-N $_5'$)-hexane dihydrochloride; 1,6-di($N_1,N_1'$-β-(p-methoxyphenyl)-diguanido-$N_5$, $N_5'$)-hexane dihydrochloride; 1,6-di($N_1,N_1'$-α-methyl-β-phenyldiguanido-$N_5,N_5'$)-hexane dihydrochloride; 1,6- di(N₁,N₁'5,N₅')-hexane dihydrochloride;ω: ω'-di-(N₁,N₁'-phenyldiguanido-N₅,N₅')di-n-propylether dihydrochloride; ω:ω'-di(N₁,N₁'-p-chlorophenyldiguanido-N₅,N₅')-di-n-propylether tetrahydrochloride; 1,6-di(N₁,Nhd 1'-2,4,5,5,N₅')hexane tetrahydrochloride; tetrahydrochloride; 1,6-di(N₁,N₁'-p-methylphenyldiguanido-N₅,N₅')-hexane dihydrochloride; 1,6-di(N₁,Nhd 1'-2,4,5,5,N₅')hexane tetrahydrochloride; 1,6-di-(N₁,N₁'-α-(p-chlorophenyl)ethyldiguanido-N₅,N₅')hexane dihydrochloride; ω:ω'-di(N₁,N₁'-p-chlorophenyldiguanido-N₅,N₅')m-xylene dihydrochloride; 1,12-di-(N₁,N₁'p-chlorophenyldiguanido-N₅,N₅')-dodecane dihydrochloride; 1,10-di(N₁,N₁'-phenyldiguanido-N₅,N₅')-decane tetrachloride; 1,12-di(N₁,N₁'-phenyldiguanido-N₅,N₅')-dodecane tetrahydrochloride; 1,6-di(N₁,N₁'-o-chlorophenyl-diguanido-N₅,N₅')hexane dihydrochloride; 1,6-di(N₁,N₁'-p-chlorophenyldiguanido-N₅,N₅')-hexane tetrahydrochloride; ethylene bis(1-tolyl biguanide); ethylene bis(p-tolyl biguanide); ethylene bis(3,5-dimethylphenyl biguanide); ethylene bis(p-tert-amylphenyl biguanide); ethylene bis(nonylphenyl biguanide); ethylene bis(phenyl biguanide); ethylene bis(N-butylphenyl biguanide); ethylene bis(2,5-diethoxyphenyl biguanide); ethylene bis(2,4-dimethylphenyl biguanide); ethylene bis(o-diphenyl biguanide); ethylene bis(mixed amyl naphthyl biguanide); N-butyl ethylene bis(phenyl biguanide); trimethylene bis (o-tolyl biguanide); N-butyl trimethylene bis(phenylbiguanide); tetramethylene bis(1-tolyl biguanide); the specific compounds disclosed in U.S. Pat. No. 2,863,919, Birtwell et al., (Dec. 9, 1958); the specific compounds disclosed in U.S. Pat. No. 3,468,898, Cutler et al., (Sept. 23, 1969); the specific compounds disclosed in U.S. Pat. No. 4,059,687, Bauman, (Nov. 22, 1977); and the corresponding pharmaceutically acceptable salts of all of the above such as the acetates, gluconates, hydrochlorides, hydrobromides, citrates, bisulfites, hydrofluorides, polymaleates, N-coconutalkyl sarcosinates, phosphites, hypophosphites, perfluorooctanoates, silicates, sorbates, salicylates, maleates, tartrates, fumarates, ethylenediaminotetraacetates, iminodiacetates, cinnamates, thiocyanates, arginates, pyromellitates, tetracarboxybutyrates, benzoates, glutarates, monofluorophosphates, and perfluoropropionates.

Preferred bisbiguanide compounds include 1,6-di(N₁,N₁'-p-chlorophenyldiguanido-N₅,N₅')hexane (chlorhexidine), 1,6-bis(2preferred bisbiguanide compound is chlorhexidine and salts thereof. Water soluble salts of chlorhexidine, alexidine and other bis-biguanide compounds are preferred, including the digluconate and the diacetate salts, especially the digluconate salts. Other preferred salts of chlorhexidine, alexidine and other bisbiguanide compounds include the dipropanate, the diformate, the dilactate, the dihydrochloride, the dihydrofluoride, the dihydrobromide, the sulfate, the phosphate, the succinate, the pivalate, the citrate, the tartrate, the maleate, the malate, the disarcosinate, the monofluorophosphate, and the hexafluorophosphate.

The present invention relates to monoperoxyphthalate compounds. As used herein, monoperoxyphthalate compounds have the structure:

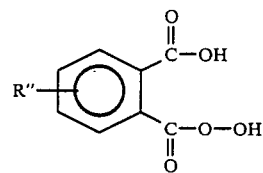

or the pharmaceutically acceptable salts or esters thereof, wherein R" may be one or more substituents compatible with the peroxy acid functionality of the aromatic ring.

By "substituents compatible with the peroxy acid functionality of the aromatic ring", as used herein, is meant substituents on the ring which do not react with peroxy acids thereby reducing the stability and effectiveness of the compounds to treat diseases of the oral cavity. Nonlimiting examples of R" groups include hydrogen, substituted and unsubstituted saturated alkyl having from 1 to about 20 carbon atoms (e.g., methyl, ethyl), substituted and unsubstituted aryl (e.g., phenyl, naphthyl), substituted and unsubstituted benzyl, chloro, fluoro, nitro, sulphonate, trifluoromethyl, trialkylammonium (e.g., trimethylammonium; triethylammonium), cyano, carboxy, carboxylate (e.g., —COOCH₃), percarboxyl (e.g., —CO₃H), and alkoxy (e.g., methoxy, ethoxy). Preferred R" groups are hydrogen, saturated alkyl having from 1 to about 20 carbon atoms, aryl, benzyl, chloro, fluoro, carboxy, and alkoxy. Particularly preferred is R" being hydrogen. R" may also be an iodo, bromo, substituted or unsubstituted amino, or amido group, but such groups are generally not desirable since they can react with peroxy acid groups. Selection of substituents compatible with the peroxy acid functionality of the aromatic ring can easily be made by one skilled in the art.

By "pharaceutically-acceptable salts or esters", as used herein, is meant esters and salts of substituted or unsubstituted monoperoxyphthalic acid compounds which have the same general antibacterial properties as the preferred magnesium salt of monoperoxyphthalic acid, and which are acceptable from a toxicity viewpoint. Nonlimiting examples of pharmaceutically-acceptable salts include alkali metal (e.g., sodium, potassium), alkaline earth metal (e.g., calcium, magnesium), non-toxic heavy metal, and tetraalkylammonium (e.g., tetraethylammonium). Preferred compounds useful in the present invention are the substituted or unsubstituted monoperoxyphthalate compounds with pharmaceutically-acceptable divalent cation salts (e.g., magnesium, calcium), and the magnesium salt being the most preferred.

Most preferred for use in the present invention is the magnesium salt of monoperoxyphthalic acid. This magnesium salt is the salt of the carboxylic acid group only, having the structure:

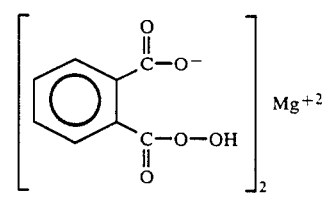

(hereinafter referred to as "PAM"), as disclosed in European Patent Application No. 27,693, published Apr. 29, 1981, filed by Interox Chemicals, Ltd., the disclosure of which is incorporated herein by reference. The compound is a hydrate when in its solid form. Synthesis of the compound is also disclosed. This compound is also commercially available from Interox Chemicals Limited.

Synthesis of substituted and unsubstituted monoperoxyphthalate compounds can be achieved by those skilled in the art using methods disclosed in, for example, in addition to European Patent Application No. 27,693, European Patent Application No. 66,992 to Interox Chemicals Ltd.; U.S. Pat. No. 3,075,921 to Brockelhurst, et al.; "Organic Peroxides", Daniel Swern, Editor, published 1970 by John Wiley and Sons, Inc.; and in British Patent Specification No. 1,378,671; the disclosures of all of which being incorporated herein by reference.

The present invention is a method for treating or preventing dental plaque, caries, or gingival or periodontal diseases of the oral cavity in humans or lower animals, with reduced staining of teeth or dentures, said method comprising topically applying to the oral surfaces of the teeth or dentures of humans or lower animals:
 (a) a safe and effective amount of a monoperoxyphthalate compound, and
 (b) a safe and effective amount of an antiplaque bis-biguanide compound.

The bis-biguanide compounds and monoperoxyphthalate compounds which are used in the methods of the present invention are generally incompatible if combined in a single composition, in that the bis-biguanide compound is oxidized and its anti-plaque activity destroyed by the monoperoxyphthalate compound. It is preferable that the bis-biguanide compound and the monoperoxyphthalate compound be provided in separate compositions which are used sequentially in the methods of the present invention. Alternatively, the bis-biguanide compound and the monoperoxyphthalate compound may preferably be incorporated in the same composition without contact, e.g., by microencapsulating one or both compounds. It is also possible to combine the bis-biguanide compound and the monoperoxyphthalate compound with contact in a single composition for use in the methods of the present invention, as long as the composition is used while there is still sufficient bis-biguanide compound to provide the desired anti-plaque activity.

In preferred methods of the present invention a monoperoxyphthalate compound and a bis-biguanide compound are used in sequence. When used in sequence, it is preferred that the monoperoxyphthalate compound be used prior to the bis-biguanide compound.

In such sequential use methods of the present invention, it is preferred that two separate compositions be used, one comprising (a) a safe and effective amount of a monoperoxyphthalate compound and (b) a pharmaceutically-acceptable carrier, and the other composition comprising (a) a safe and effective amount of an anti-plaque bis-biguanide compound and (b) a pharmaceutically-acceptable carrier. The pharmaceutically-acceptable carriers of each composition are preferably in the form of any of a number of conventional oral care products, for example, a solution (e.g., mouthrinse, mouth spray), a dentifrice (e.g., toothpaste, gel or tooth powder), chewing gum, chewable tablets, lozenge or sachet. Preferred compositions useful in the methods of the present invention are one composition being in the form of a solution and the other being in the form of a dentifrice, or both compositions being in the form of solutions.

When the bis-biguanide compound and the monoperoxyphthalate compound are incorporated in the same composition, it is preferred that these active compounds be incorporated in such compositions without contact, (e.g., by encapsulating one or both of the active compounds by any method known to skilled artisans), unless the composition is to be used shortly after it is made. Therefore, preferred compositions of the present invention are in the form of oral compositions and comprise:
 (a) a safe and effective amount of a monoperoxyphthalate compound,
 (b) a safe and effective amount of an anti-plaque bis-biguanide compound, and
 (c) a pharmaceutically-acceptable carrier, whereby the monoperoxyphthalate compound and the anti-plaque bis-biguanide compound are incorporated in the composition without contact.

The pharmaceutically-acceptable carriers for such compositions of the present invention are preferably in the form of conventional oral care products, for example, a suspension (e.g., mouthrinse), a dentifrice (e.g., toothpaste, gel or tooth powder), chewing gum, chewable tablets, lozenge or sachet.

Other preferred compositions of the present invention comprise:
 (a) a safe and effective amount of a monoperoxyphthalate compound,
 (b) a safe and effective amount of an anti-plaque bis-biguanide compound, and
 (c) a pharmaceutically-acceptable carrier.

The pharmaceutically-acceptable carriers of such compositions are preferably in the form of a conventional oral care product, for example, a solution (e.g., mouthrinse, mouth spray). Such a solution is preferably prepared shortly prior to its use by adding one of the active compounds to a pharmaceutically-acceptable carrier containing the other active compound, or by adding both active compounds separately to a pharmaceutically-acceptable carrier.

The compositions useful in the present invention which comprise a bis-biguanide compound, whether or not in combination with a monoperoxyphthalate compound, preferably comprise from about 0.001% to about 4% of the bis-biguanide compound, more preferably from about 0.01% to about 1%, most preferably from about 0.03% to about 0.2%. In the methods of the present invention, such bis-biguanide composition is preferably used from about once to about four times daily, more preferably once or twice daily, most preferably twice daily. In the methods of the present invention, such bis-biguanide composition is in contact with the dental surfaces in the oral cavity for from about one second to about 300 seconds during each use, more preferably for from about 10 seconds to about 120 seconds during each use, most preferably for from about 30 seconds to about 60 seconds during each use.

The compositions useful in the present invention which comprise a monoperoxyphthalate compound, whether or not in combination with a bis-biguanide compound, preferably comprise from about 0.01% to about 10% of the monoperoxyphthalate compound, more preferably from about 0.25% to about 5%, most preferably from about 1% to about 4%. In the methods of the present invention, such monoperoxyphthalate composition is preferably used from about once to about four times daily, more preferably once or twice daily, most preferably twice daily. In the methods of the present invention, such monoperoxyphthalate composition is in contact with the dental surfaces in the oral cavity for from about one second to about 300 seconds during each use, more preferably for from about 10 seconds to about 120 seconds during each use, most preferably for from about 30 seconds to about 60 seconds during each use.

The methods of the present invention generally result in unexpected benefits both in anti-plaque activity and in reduced staining of teeth. The use of either a bis-biguanide compound or a monoperoxyphthalate compound alone results in a reduction or inhibition of plaque in humans or lower animals. The methods of the present invention, where both a bis-biguanide compound and monoperoxyphthalic compound are used, generally result in a synergistic reduction or inhibition of plaque compared to the separate use of either compound alone.

The substantial staining of teeth by bis-biguanide compounds is well-known. The use of monoperoxyphthalate compounds also results in some staining of teeth, although substantially less than due to the use of bis-biguanide compounds. (See U.S. Pat. No. 4,716,035, column 14, Table 2, lines 50–64.) Surprisingly, the combined use the bis-biguanide compounds and monoperoxyphthalate compounds generally results in no more staining of teeth than the use of the monoperoxyphthalate compounds alone.

For the preferred sequential use methods of the present invention, it has been surprisingly found that unexpected benefits of synergistic reduction or inhibition of plaque and reduced staining are in general relatively independent of the timing of the use of the monoperoxyphthalate composition and the bis-biguanide composition. Thus the methods are generally about equally effective whether these compositions are used only minutes apart or several hours apart. It is preferred that the monoperoxyphthalate composition be used from about 30 seconds to about 18 hours, more preferably from about 1 minute to about 12 hours, more preferably still from about 2 minutes to about 30 minutes, prior to the use of the bis-biguanide composition.

The following non-limiting examples are exemplary of compositions useful in and methods of the present invention.

EXAMPLE 1

A toothpaste is made using the procedure taught in U.S. Pat. No. 3,988,433 issued to Benedict on Oct. 26, 1976, which is hereby incorporated herein by reference. The composition of the toothpaste is as follows:

| Component | Wt. % |
| --- | --- |
| Sodium Saccharin | 0.25 |
| PAM | 4.00 |
| Sodium Laurel Sulfate | 2.68 |
| Sodium Fluoride | 0.33 |
| Titanium Dioxide | 1.34 |
| Cabosil | 3.52 |
| Silica | 20.09 |
| Peppermint Oil | 2.00 |
| Anethol (licorice) Oil | 1.00 |
| Sodium Bicarbonate | 1.00 |
| Mineral Oil | Balance |

EXAMPLE 2

A mouthrinse solution is made by dissolving components in water by mixing. The composition of the mouthrinse is as follows:

| Component | Wt. % |
| --- | --- |
| Chlorhexidine Digluconate | 0.12 |
| Ethanol (95%) | 10.00 |
| Glycerin | 8.00 |
| PEG-40 SDIS (polyethylene glycol sorbitan diisostearate) | 0.17 |
| Spearmint Flavor | 0.08 |
| Sodium Saccharin | 0.01 |
| Color FD&C Blue #1 (1% solution) | 0.011 |
| Water | Balance |

EXAMPLE 3

Using one gram of the dentifrice of Example 1, a person brushes his teeth for thirty seconds, rinsing with water. Ten minutes later, he rinses his mouth and teeth using 10 ml of the mouthrinse of Example 2 for 10 seconds. This regimen repeated twice daily inhibits the formation of plaque on the person's teeth.

EXAMPLE 4

A powder composition is made by dry blending the following components:

| Component | Wt. % |
| --- | --- |
| PAM | 45 |
| Sodium Bicarbonate | 44 |
| Peppermint Flavor (spray dried) | 1 |
| Sodium Saccharin | 10 |

EXAMPLE 5

A person having periodontal disease dissolves 0.2 gram of the powder composition of Example 4 in 10 ml of water. He rinses his mouth and teeth with the resulting solution for 60 seconds. Four hours later, he rinses his mouth and teeth using 5 ml of the mouthrinse of Example 2 for 60 seconds. This regimen repeated twice daily reduces the severity of the periodontal disease of the person in one month.

While particular embodiments of the present invention have been described, it will be obvious to those skilled in the art that various changes and modifications to the methods disclosed herein can be made without departing from the spirit and scope of the invention. It is intended to cover, in the appended claims, all such modifications that are within the scope of this invention.

What is claimed is:

1. A method for treating or preventing dental plaque, or gingival or periodontal diseases of the oral cavity in humans or lower animals, said method comprising topically applying to the oral surfaces of the teeth or dentures of humans or lower animals:

(a) a safe and effective amount of a monoperoxyphthalate compound having the structure:

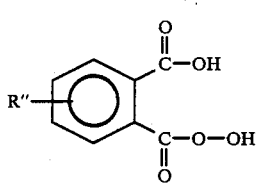

or the pharmaceutically acceptable salts or esters thereof, wherein R'' is one or more substituents compatible with the peroxy acid functionality of the aromatic ring; and (b) a safe and effective amount of an anti-plaque bis-biguanide compound having the structure:

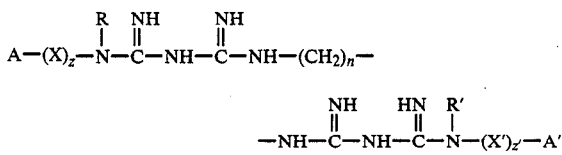

or the pharmaceutically-acceptable salts thereof, wherein A and A' each represent either (1) a phenyl radical which optionally is substituted by an alkyl or alkoxy group containing from 1 to about 4 carbon atoms, a nitro group, or a halogen atom; (2) an alkyl group containing from 1 to about 12 carbon atoms; or (3) alicyclic groups containing from 4 to about 12 carbon atoms; X and X' each represent an alkylene radical containing from 1 to 3 carbon atoms; z and z' each can be either 0 or 1; R and R' each represent either hydrogen, an alkyl radical containing from 1 to about 12 carbon atoms, or an aralkyl radical containing from 7 to about 12 carbon atoms; n is an integer from 2 to 12 inclusive.

2. The method of claim 1 wherein R'' is selected from the group consisting of hydrogen, substituted and unsubstituted saturated alkyl having from 1 to about 20 carbon atoms, substituted and unsubstituted aryl, substituted and unsubstituted benzyl, chloro, fluoro, nitro, sulfonate, trifluoromethyl, trialkylammonium, cyano, carboxy, carboxylate, percarboxy, and alkoxy.

3. The method of claim 2 wherein R'' is selected from group consisting of hydrogen, saturated alkyl having from 1 to about 20 carbon atoms, phenyl, benzyl, chloro, fluoro, carboxy, and alkoxy.

4. The method of claim 3 wherein R'' is hydrogen.

5. The method of claim 1 wherein the monoperoxyphthalate compound has the structure

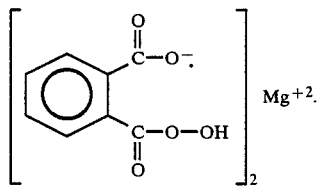

6. The method of claim 1 wherein the bis-biguanide compound is chlorhexidine or alexidine.

7. The method of claim 3 wherein the bis-biguanide compound is chlorhexidine or alexidine.

8. The method of claim 4 wherein the bis-biguanide compound is chlorhexidine.

9. The method of claim 5 wherein the bis-biguanide compound is chlorhexidine digluconate.

10. The method of claim 1 wherein two separate compositions are applied in sequence, one composition comprising the monoperoxyphthalate compound and a pharmaceutically-acceptable carrier, and the other composition comprising the bis-biguanide compound and a pharmaceutically-acceptable carrier.

11. The method of claim 3 wherein two separate compositions are applied in sequence, one composition comprising the monoperoxyphthalate compound and a pharmaceutically-acceptable carrier, and the other composition comprising the bis-biguanide compound and a pharmaceutically-acceptable carrier.

12. The method of claim 7 wherein two separate compositions are applied in sequence, one composition comprising the monoperoxyphthalate compound and a pharmaceutically-acceptable carrier, and the other composition comprising the bis-biguanide compound and a pharmaceutically-acceptable carrier.

13. The method of claim 8 wherein two separate compositions are applied in sequence, one composition comprising the monoperoxyphthalate compound and a pharmaceutically-acceptable carrier, and the other composition comprising the bis-biguanide compound and a pharmaceutically-acceptable carrier.

14. The method of claim 9 wherein two separate compositions are applied in sequence, one composition comprising the monoperoxyphthalate compound and a pharmaceutically-acceptable carrier, and the other composition comprising the bis-biguanide compound and a pharmaceutically-acceptable carrier.

15. The method of claim 12 wherein the monoperoxyphthalate compound comprises from about 0.25% to about 5% of the monoperoxyphthalate composition, and the bis-biguanide compound comprises from about 0.01% to about 1% of the bis-biguanide composition.

16. The method of claim 14 wherein the monoperoxyphthalate compound comprises from about 1% to about 4% of the monoperoxyphthalate composition, and the bis-biguanide compound comprises from about 0.03% to about 0.2% of the bis-biguanide composition.

17. The method of claim 15 wherein one of the compositions is in the form of a mouthrinse solution, and the other composition is in the form of a dentifrice or a mouthrinse solution, each composition is used once or twice daily, and the monoperoxyphthalate composition is used from about 30 seconds to about 12 hours prior to the use of the bis-biguanide composition.

18. The method of claim 16 wherein one of the compositions is in the form of a mouthrinse solution, and the other composition is in the form of a dentifrice or a mouthwash solution, each composition is used once or twice daily, and the monoperoxyphthalate composition is used from about 30 seconds to about 12 hours prior to the use of the bis-biguanide composition.

19. The method of claim 18 wherein the monoperoxyphthalate composition is used from about 30 seconds to about 30 minutes prior to the use of the bis-biguanide composition.

20. A composition comprising:
(a) a safe and effective amount of a monoperoxyphthalate compound according to claim 1,
(b) a safe and effective amount of an anti-plaque bis-biguanide compound according to claim 1, and
(c) a pharmaceutically-acceptable carrier.

21. The composition of claim 20 wherein the monoperoxyphthalate compound and the bis-biguanide compound are incorporated in the composition without contact.
22. The composition of claim 20 wherein R" is hydrogen and the bis-biguanide compound is chlorhexidine or alexidine.
23. The composition of claim 20 wherein the bis-biguanide compound is chlorhexidine digluconate, and the monoperoxyphthalate compound has the structure
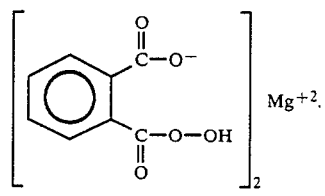
* * * * *

UNITED STATES PATENT AND TRADEMARK OFFICE
CERTIFICATE OF CORRECTION

PATENT NO. : 4,886,658
DATED : December 12, 1989
INVENTOR(S) : Duane L. Charbonneau, Debra J. Moore and Joel I. Shulman It is certified that error appears in the above-identified patent and that said Letters Patent is hereby corrected as shown below:

In Column 3, line 1, "di($N_1,N_1$'5,$N_5$')-hexane dihydrochloride;ω: ω'-di-($N_1$," should be --di($N_1,N_1$'-p-nitrophenyldiguanido-$N_5N_5$')-hexane dihydrochloride; ω:ω'-di-($N_1$,--.

In Column 3, line 2, "$N_5$')di" should be --$N_5$')-di--.

In Column 3, line 5, "di($N_1$,Nhd 1'-2,4,5,5,$N_5$')hexane" should be --di($N_1,N_1$'-2,4-dichlorophenyldiguanido-$N_5,N_5$')hexane--.

In Column 3, line 6, delete --tetrahydrochloride;--. (2nd Occur.)

In Column 3, line 8, "di($N_1$Nhd 1'-2,4,5,5,$N_5$')hexane" should be --di($N_1,N_1$'-2,4,5-trichlorophenyldiguanido-$N_5,N_5$')hexane--.

In Column 3, line 48, "1,6-bis(2preferred" should be --1,6-bis(2-ethylhexyldiguanidohexane)(alexidine), and salts thereof. Most preferred--.

Signed and Sealed this

Tenth Day of September, 1991

Attest:

HARRY F. MANBECK, JR.

Attesting Officer

Commissioner of Patents and Trademarks